(12) United States Patent
Constantineau et al.

(10) Patent No.: US 9,675,785 B2
(45) Date of Patent: Jun. 13, 2017

(54) FOLDING INSERTER FOR DRUG DELIVERY INFUSION SET

(75) Inventors: Cole Constantineau, Cambridge, MA (US); Ryan Schoonmaker, San Marcos, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 932 days.

(21) Appl. No.: 13/983,984

(22) PCT Filed: Feb. 8, 2012

(86) PCT No.: PCT/US2012/000075
§ 371 (c)(1),
(2), (4) Date: Oct. 17, 2013

(87) PCT Pub. No.: WO2012/108959
PCT Pub. Date: Aug. 16, 2012

(65) Prior Publication Data
US 2014/0163523 A1    Jun. 12, 2014

Related U.S. Application Data

(60) Provisional application No. 61/441,208, filed on Feb. 9, 2011.

(51) Int. Cl.
*A61M 25/06* (2006.01)
*A61M 5/158* (2006.01)

(52) U.S. Cl.
CPC ........ *A61M 25/0631* (2013.01); *A61M 5/158* (2013.01); *A61M 25/0606* (2013.01); *A61M 2005/1585* (2013.01)

(58) Field of Classification Search
CPC .......... A61M 5/158; A61M 2005/1585; A61M 2005/1586; A61M 2005/1587
See application file for complete search history.

(56) References Cited

U.S. PATENT DOCUMENTS 5,562,629 A * 10/1996 Haughton ............. A61M 5/158
604/158
5,584,813 A * 12/1996 Livingston ........ A61M 25/0637
604/177

(Continued)

*Primary Examiner* — Laura Bouchelle
(74) *Attorney, Agent, or Firm* — Dickinson Wright PLLC

(57) ABSTRACT

An infusion set (101) includes an inserter (121) pivotally connected to a base (111). The inserter (121) includes a catheter (173) and an introducer needle (167). The catheter (173) is movable from a first catheter position disposed substantially entirely within the inserter (121) to a second catheter position in which a free end of the catheter (173) is disposed externally of the inserter (121) and the base (111). The introducer needle (167) is movable between a first introducer needle position disposed substantially entirely within the inserter (121) and a second introducer needle position in which a free end of the introducer needle (167) is disposed externally of the inserter (121) and the base (111). An activation button (141) is movable between first and second button positions. When the button (141) is moved from the first button position to the second button position, the catheter (173) is moved from the first to the second catheter position, and the introducer needle (167) is moved from the first to the second introducer needle position to facilitate insertion of the catheter (173) and back to the first introducer needle position to store the introducer needle (167) within the inserter (121). The inserter (121) is then pivotable from an insertion position to a storage position within the base (111) of the infusion set (101).

20 Claims, 11 Drawing Sheets

(56) References Cited

U.S. PATENT DOCUMENTS

| | | | |
|---|---|---|---|
| 6,086,575 A * | 7/2000 | Mejslov | A61M 5/158 604/533 |
| 6,579,267 B2 | 6/2003 | Lynch | |
| 7,083,597 B2 | 8/2006 | Lynch | |
| 7,214,207 B2 | 5/2007 | Lynch | |
| 7,766,867 B2 | 8/2010 | Lynch | |
| 7,862,545 B2 | 1/2011 | Lynch | |
| 2003/0216686 A1 | 11/2003 | Lynch | |
| 2004/0158207 A1 | 8/2004 | Hunn | |
| 2006/0200073 A1 | 9/2006 | Radmer | |
| 2007/0149920 A1 | 6/2007 | Michels | |
| 2007/0173767 A1 | 7/2007 | Lynch | |
| 2007/0191772 A1 | 8/2007 | Wojcik | |
| 2007/0191773 A1 | 8/2007 | Wojcik | |
| 2009/0088722 A1 | 4/2009 | Wojcik | |
| 2009/0254041 A1 | 10/2009 | Krag | |

* cited by examiner

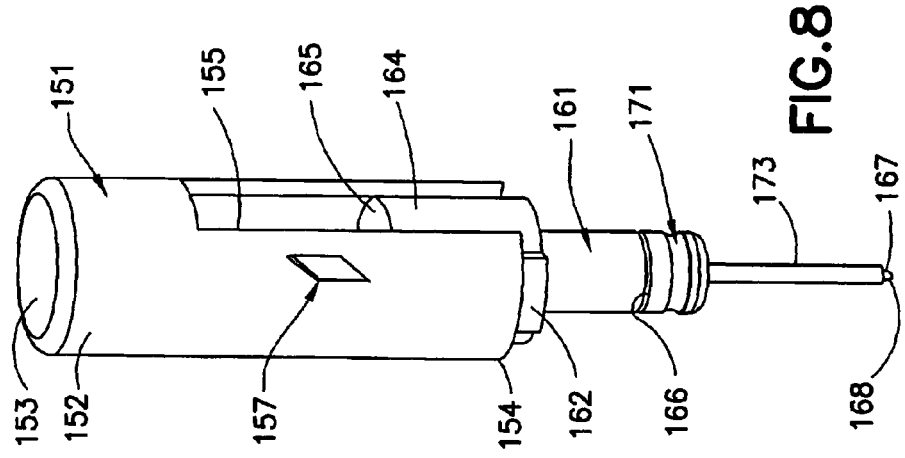
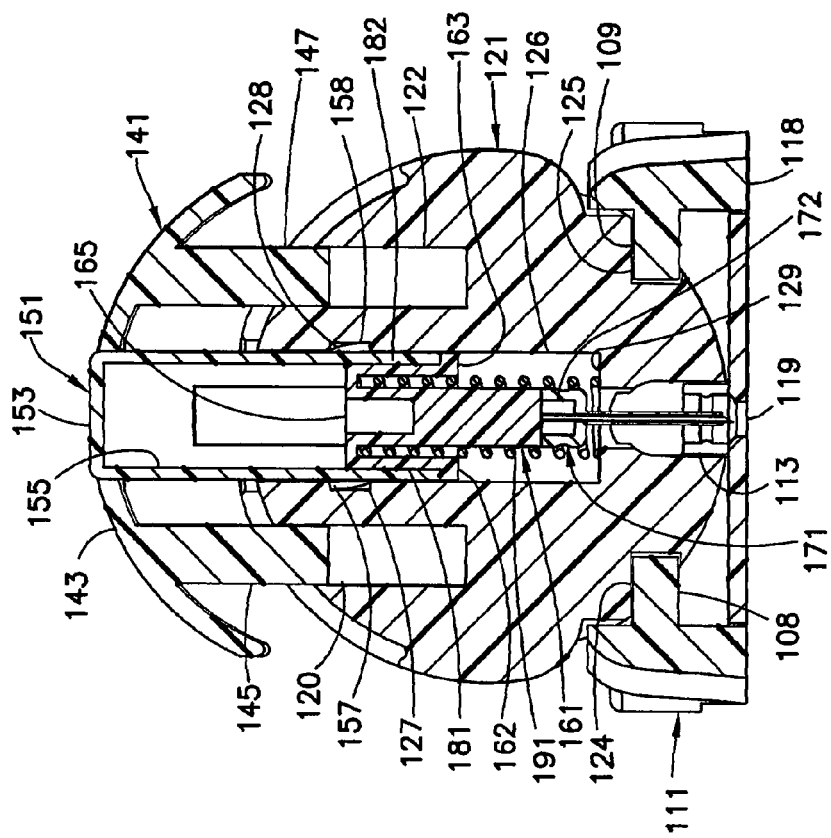

FOLDING INSERTER FOR DRUG DELIVERY INFUSION SET

CROSS REFERENCE TO RELATED APPLICATION

This application claims the benefit under 35 U.S.C. §119 (e) of U.S. Provisional Application Ser. No. 61/441,208, filed on Feb. 9, 2011, which is hereby incorporated by reference in its entirety.

FIELD OF THE INVENTION

The present invention relates generally to an infusion set having a folding inserter. More particularly, the present invention relates to a self-contained, folding inserter in which an introducer needle is stored in a base after being withdrawn from an insertion site. Still more particularly, the present invention relates to a self-contained, folding inserter in which an introducer needle and catheter are inserted at an insertion site and the introducer needle is withdrawn from the insertion site by the push of an activation button, and the inserter is foldable into a body with the introducer needle stored substantially entirely within the inserter.

BACKGROUND OF THE INVENTION

A large number of people with diabetes use some form of daily insulin therapy to maintain close control of their glucose levels. Currently, there are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. Infusion pumps, although more complex than syringes and pens, offer the advantages of continuous infusion of insulin, precision dosing and programmable delivery schedules. This results in closer blood glucose control and an improved feeling of wellness.

The use of an infusion pump requires the use of a disposable component, typically referred to as an infusion set, tubing set or pump set, which conveys the insulin from a reservoir within the pump into the skin of the user. An infusion set typically consists of a pump connector, a length of tubing, and a hub or base from which an infusion needle or catheter extends. The hub or base has an adhesive that retains the base on the skin surface during use. The hub or base may be applied to the skin manually or with the aid of a manual or automatic insertion device. Often, the insertion device is a separate, stand-alone unit that the user is required to carry and provide.

There are many available types of infusion sets, including steel catheter infusion sets and soft catheter sets. Soft catheter sets are typically inserted into a patient manually with the aid of a steel introducer needle, which is later removed from the patient leaving the soft catheter in place. In another type of infusion set, as noted above, a mechanized inserter is used to insert the introducer needle and catheter, remove the introducer needle, or both. The introducer needle is completely removed from the infusion set before the infusion set is connected to the insulin pump.

As noted above, the user typically must remove the introducer needle after inserting a soft catheter infusion set. This can expose the user to accidental needle sticks from handling the removed introducer needle.

Accordingly, a need exists for an infusion set that facilitates insertion of the catheter, while reducing the number of components a user must carry and substantially preventing accidental needle sticks.

SUMMARY OF THE INVENTION

An object of the present invention is to provide an infusion set that includes an integral introducer needle to facilitate catheter insertion.

Another object of the present invention is to provide an infusion set having an integral folding introducer needle to facilitate catheter insertion and reduce the number of components a user must carry.

Another object of the present invention is to provide an infusion set having an integrated folding introducer needle to substantially reduce the overall size of the infusion set.

In accordance with exemplary embodiments of the present invention, a drug delivery infusion set houses and stores an introducer needle and the means to insert and retract the introducer needle. A soft catheter and the introducer needle are manually inserted from a vertical position of the inserter. The introducer needle is automatically and fully retracted with the inserter in the vertical position. The inserter is then pivoted to a horizontal position to be stored in the base of the infusion set. Because the introducer needle is stored in the base of the infusion set, the user does not have to manually remove the introducer needle. Thus, user contact with the introducer needle is avoided, thereby preventing accidental introducer needle sticks. Additionally, because the introducer needle is fully retracted from the soft catheter, the introducer needle is not part of the fluid path, thereby substantially preventing leakage and sealing problems.

An infusion set in accordance with exemplary embodiments of the present invention includes a base and an inserter pivotally connected to the base. The inserter includes a catheter movable from a first catheter position disposed substantially entirely within the inserter to a second catheter position in which a free end of the catheter is disposed externally of the inserter and the base. An introducer needle located within the catheter and movable between a first introducer needle position disposed substantially entirely within the inserter and a second introducer needle position in which a free end of the introducer needle is disposed externally of the inserter and the base. An activation button is movable between first and second button positions. When the button is moved from the first button position to the second button position, the catheter is moved from the first to the second catheter position, the introducer needle is moved from the first to the second introducer needle position to facilitate insertion of the catheter, and the introducer needle is thereafter moved back to the first introducer needle position to store the introducer needle within the inserter with the free end of the catheter remaining disposed externally of the inserter and the base.

A method of inserting a catheter of an infusion set in accordance with exemplary embodiments of the present invention includes disposing the infusion set on a skin surface at an injection site. An introducer needle and the catheter are inserted through the skin surface with an inserter of the infusion set. The inserted introducer needle is then removed from the skin surface. The removed introducer needle is stored substantially entirely within the inserter. The inserter is pivoted from a substantially vertical to a substantially horizontal position to store the inserter within a base of the infusion set.

As used in this application, the terms "front," "rear," "upper," "lower," "upwardly," "downwardly," and other orientational descriptors are intended to facilitate the description of the exemplary embodiments of the present invention, but are not intended to limit the structure thereof to any particular position or orientation.

BRIEF DESCRIPTION OF THE DRAWINGS

The various objects, benefits, advantages and salient features of the present invention will become more apparent from the following detailed description of exemplary embodiments thereof and from the accompanying drawing figures, in which:

FIG. 7 is a front elevational in cross-section of the inserter and base of FIG. 1;

FIG. 8 is a perspective view of the sleeve and an introducer hub of FIG. 7;

Throughout the drawings, like reference numerals will be understood to refer to like parts, components and structures.

DETAILED DESCRIPTION OF THE EXEMPLARY EMBODIMENTS

Figure 21:
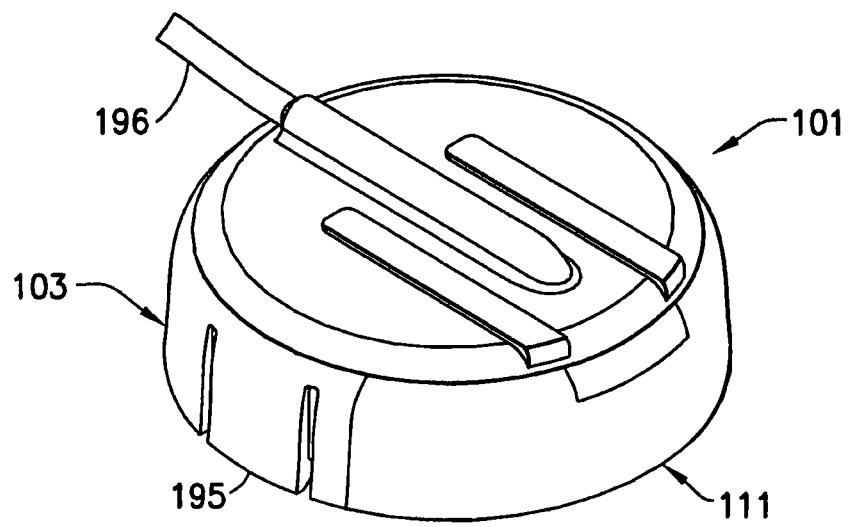
FIG. 21 is a perspective view of the assembled infusion set of FIG. 20 in which the fluid connector is connected to the inserter and base of the infusion set.
Figure 20:
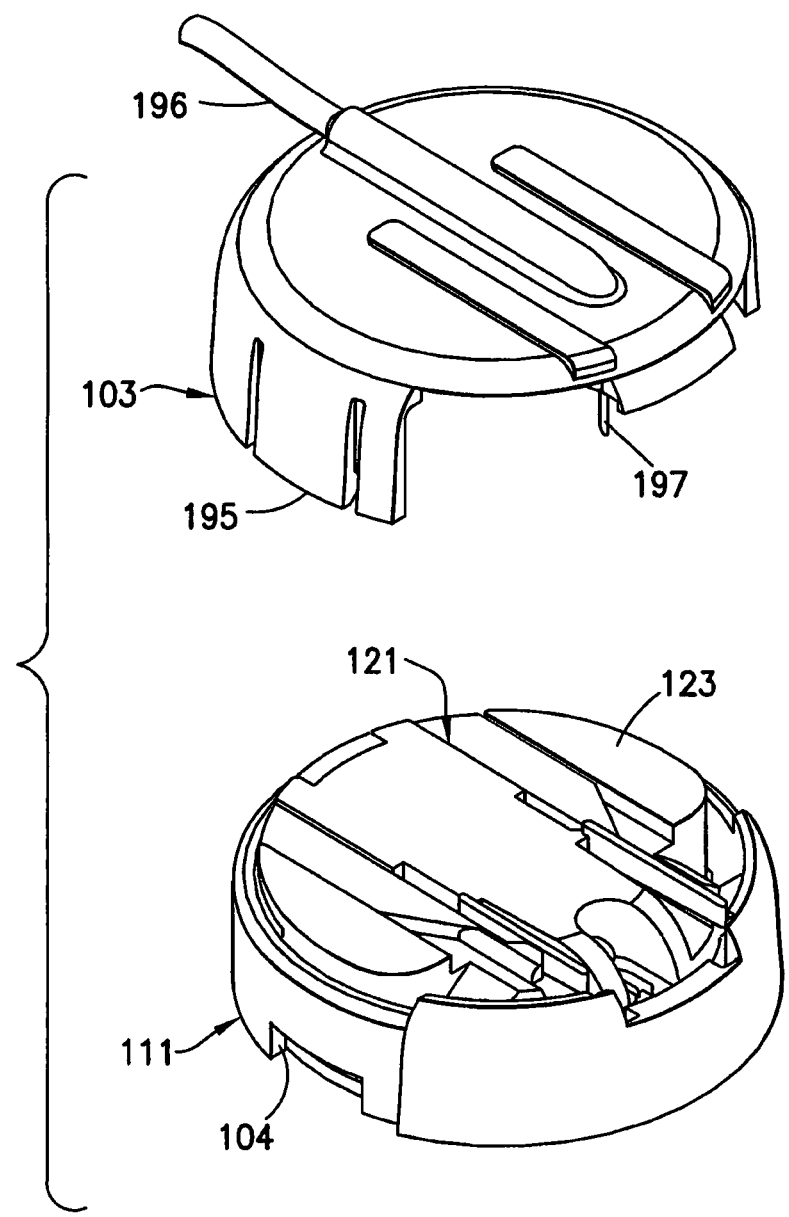
FIG. 20 is a perspective view of the inserter folded into the base of an infusion set of FIG. 17 prior to a fluid connector being connected thereto.

The exemplary embodiments of the present invention described below provide a novel means of inserting an infusion catheter into the skin. For example, exemplary embodiments of the present invention provide a folding inserter 121 that inserts a soft catheter 173 into the skin, withdraws a hollow introducer needle 167, and then folds into a base 111 of an infusion set 101, as shown in FIGS. 20 and 21, thereby providing a low profile infusion set 101.

The base 111 of the infusion set 101 is preferably provided with a skin-securing, adhesive layer 110 to secure the infusion set to the skin surface at the insertion site. The adhesive layer 110 ensures that the base 111 is at the proper position relative to the skin surface, and that the skin is secured during insertion to further aid introducer needle 167 insertion with a reduced risk of tenting of the skin surface. For clarity, the adhesive layer 110 is shown in FIG. 1, and is omitted from the remaining drawing figures.

Figure 1:
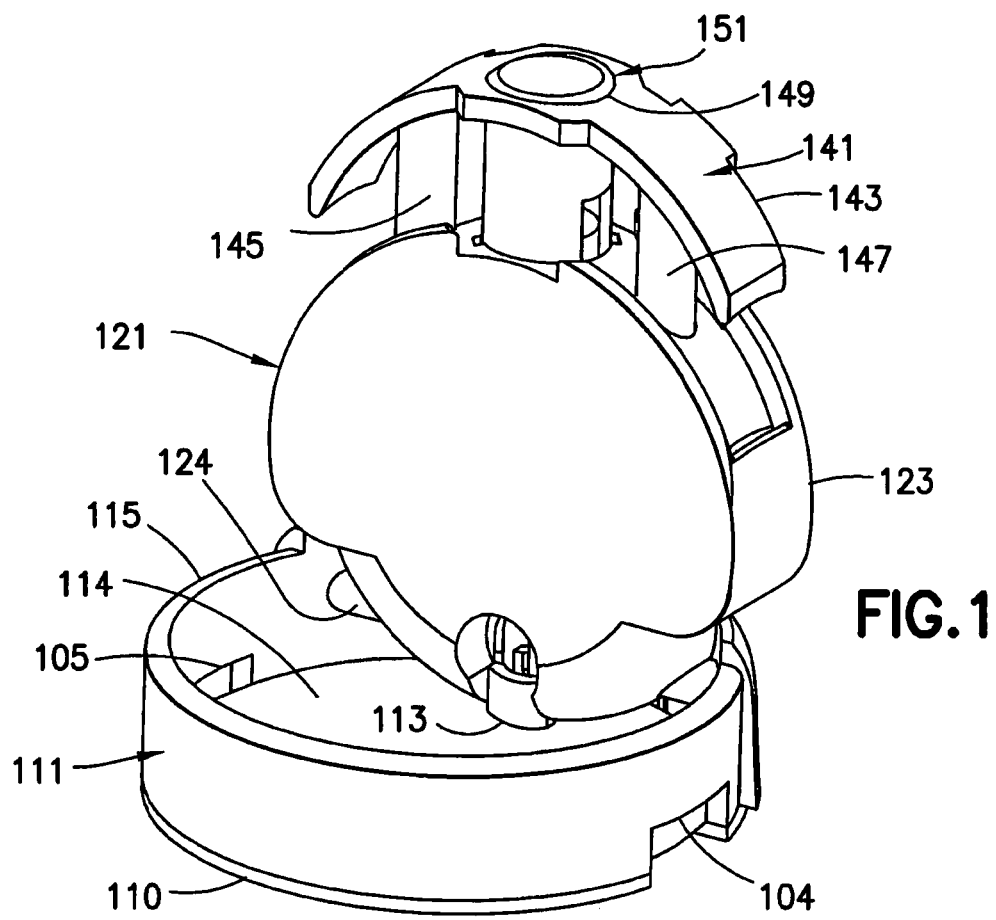
FIG. 1 is a perspective view of a folding inserter and base in accordance with an exemplary embodiment of the present invention.
Figure 2:
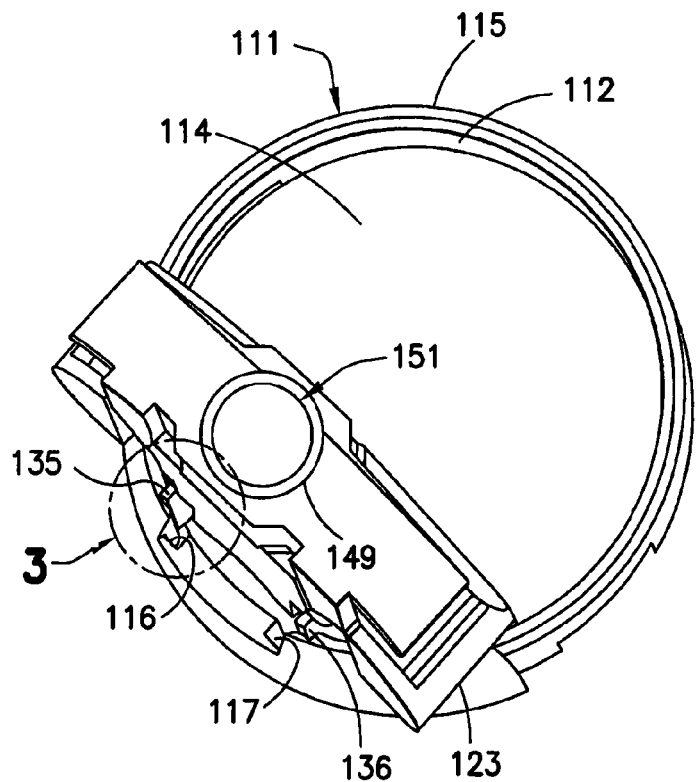
FIG. 2 is a perspective view of the inserter and base of FIG. 1.
Figure 3:
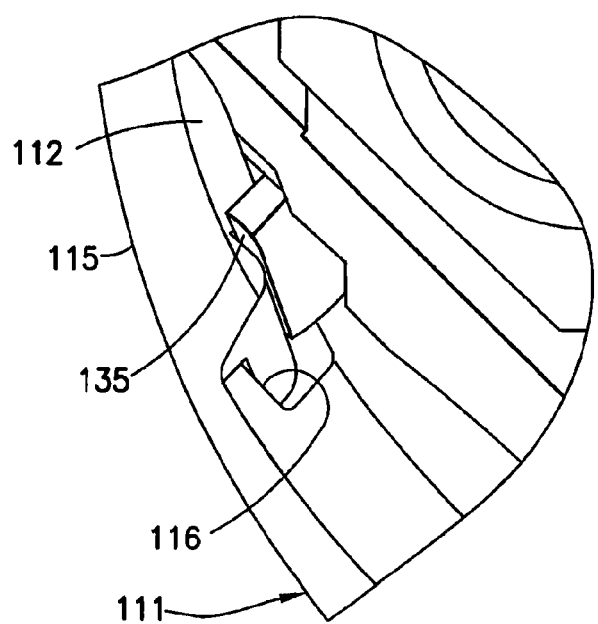
FIG. 3 is an enlarged partial view of the inserter of FIG. 2.
Figure 5:
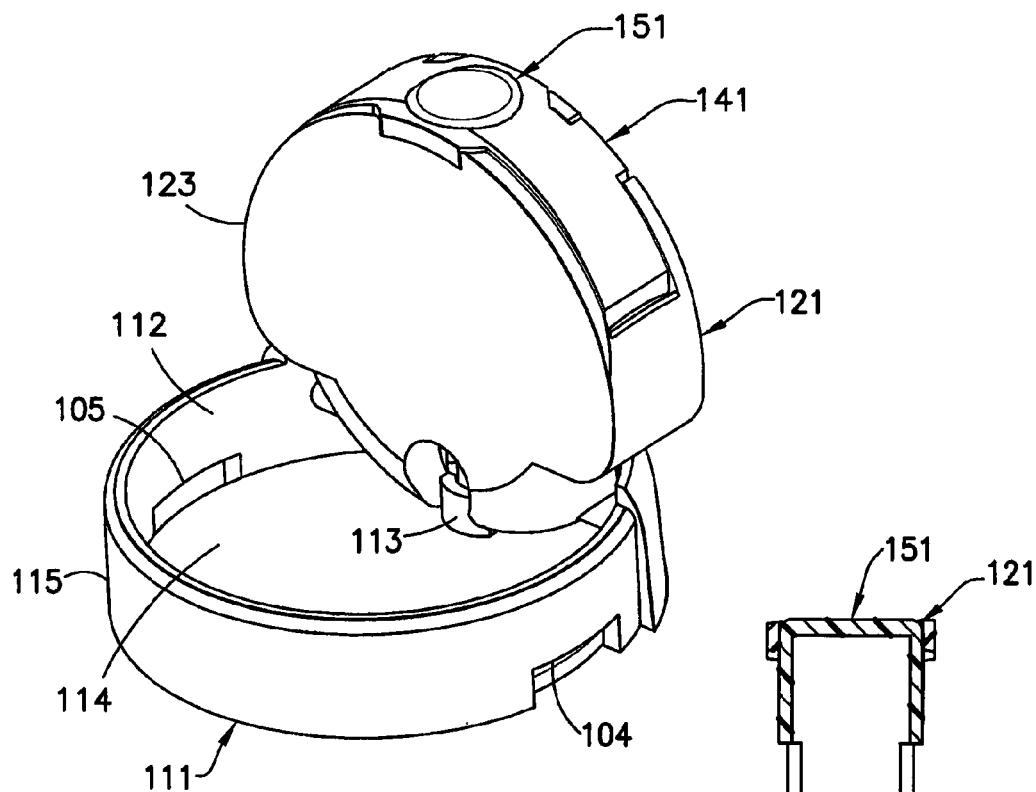
FIG. 5 is a perspective view of the inserter and base of FIG. 1 with an activation button in the depressed position.
Figure 9:
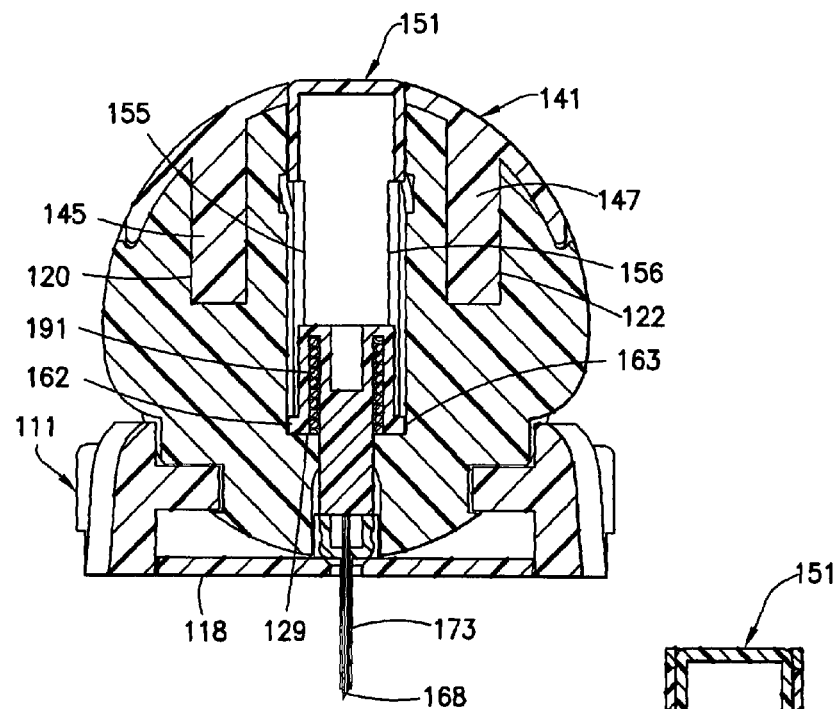
FIG. 9 is a front elevational in cross-section of the inserter and base of FIG. 1 with the activation button in the depressed position to insert an introducer needle and a soft catheter into an insertion site.
Figure 10:
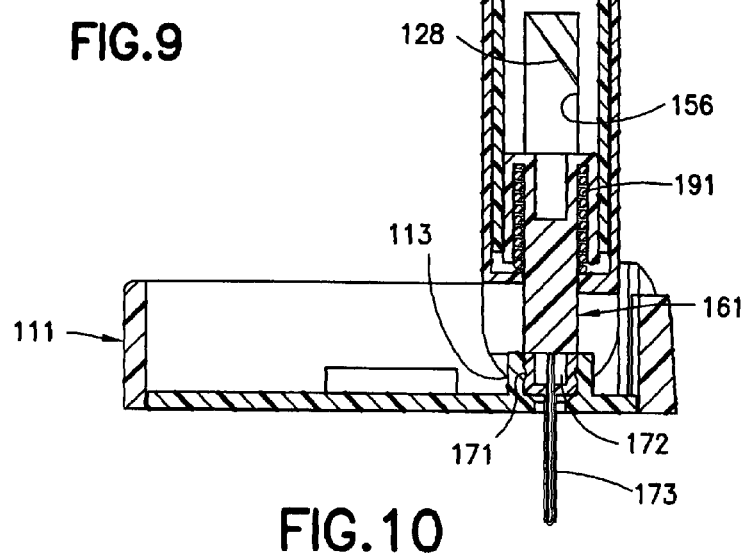
FIG. 10 is a side elevational view in cross-section of the inserter and base of FIG. 9.

The base has an inner surface 114 from which a wall 115 extends upwardly, as shown in FIGS. 1 and 2. A projection 113 extends upwardly from the inner surface 114 of the base 111 and has an opening 119 extending to the lower surface 118 of the base to allow the introducer needle 167 and soft catheter 173 to pass therethrough, as shown in FIGS. 7, 9 and 10. First and second grooves 116 and 117 are formed in the wall 115, as shown in FIGS. 2 and 3, and extend perpendicularly with respect to the inner surface 114. First and second openings 104 and 105 are formed in the wall 115, as shown in FIGS. 1 and 5.

Figure 4:
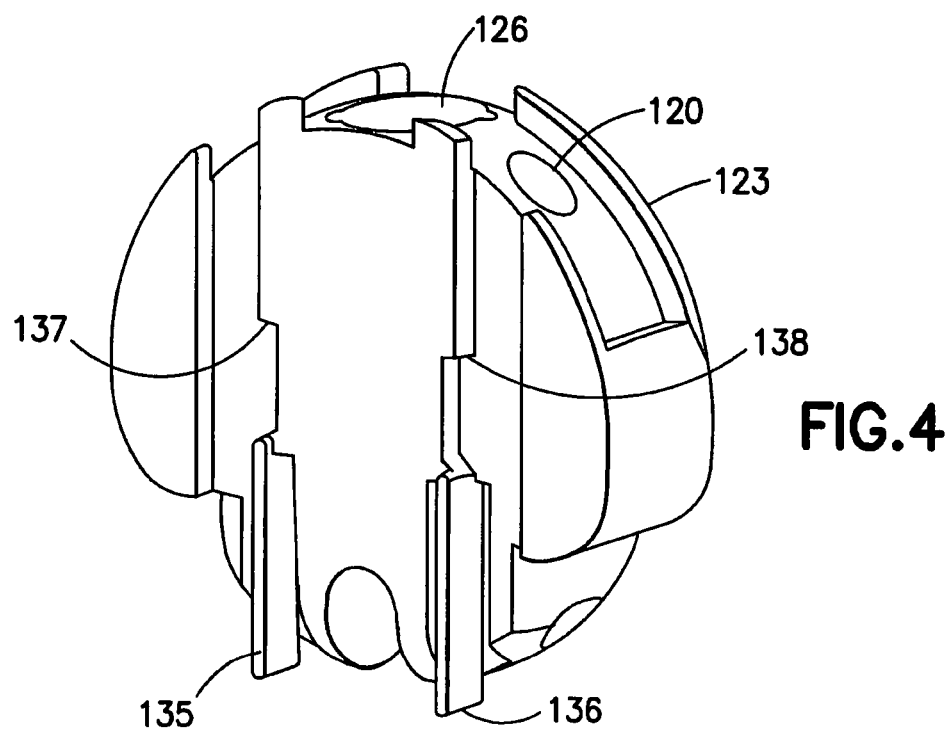
FIG. 4 is a rear perspective view of the inserter of FIG. 1.

The folding inserter 121 includes an inserter body 123 that pivots about the projection base 113, as shown in FIGS. 1 and 16-19. The body 123 has first and second downwardly extending cavities 120 and 122 adapted to receive first and second button posts 145 and 147, as shown in FIG. 7. A bore 126 extends completely through the inserter body 123, as shown in FIG. 7. Diametrically opposed threads 127 and 128 are formed in the bore 126 and receive sleeve tabs 157 and 158 to guide downward movement of a sleeve 151, as shown in FIGS. 7 and 8. First and second flexible arms 135 and 136 extend downwardly from the body 123, as shown in FIGS. 2-4.

Pins 108 and 109 extend inwardly from an inner surface of the wall 115, as shown in FIG. 7. The pins 108 and 109 are received by recesses 124 and 125 in the body 123 of the inserter 121, thereby allowing the inserter to pivot about the pins. Accordingly, the inserter 121 can pivot from a vertical, or first position, as shown in FIG. 1 to a second, or horizontal position, shown in FIGS. 17-19.

Figure 15:
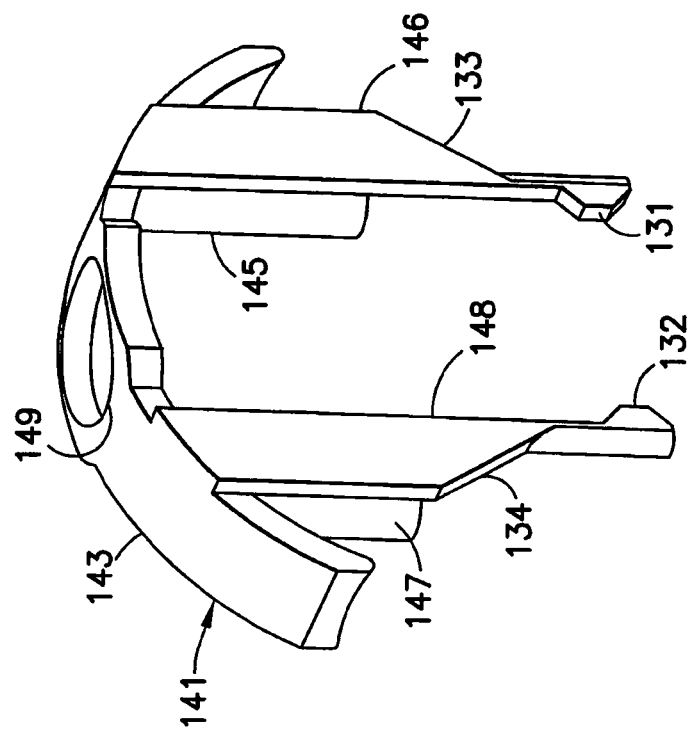
FIG. 15 is a perspective view of the activation button of FIG. 1.

An activation button 141 has a base 143 from which the first and second button posts 145 and 147 extend downwardly, as shown in FIGS. 1 and 7. Preferably, the base 143 has a substantially arcuate shape. An opening 149 is formed in the base 143, as shown in FIG. 15, to receive a first end 153 of a sleeve 151. First and second flexible arms 146 and 148 extend downwardly from the base 143, as shown in FIG. 15. Inwardly facing hooks 131 and 132 are formed at free ends of the button arms 146 and 148. The hooks 131 and 132 engage shoulders 137 and 138 in the inserter body 123, as shown in FIG. 4, to prevent the activation button 141 from being withdrawn. Ramped surfaces 133 and 134 are formed on the button arms 146 and 148 and face outwardly. The ramped surfaces 133 and 134 taper outwardly from the free ends of the arms 146 and 148 toward the fixed ends.

The sleeve 151 has a first end 153 received by the opening 149 in the activation button 141 and a wall 155 extending downwardly therefrom, as shown in FIGS. 7 and 8. The second end 154 of the sleeve 151 is open to receive an introducer hub 161. First and second recesses 155 and 156 are formed in the wall 155, as shown in FIGS. 8-10. Tabs 157 and 158 extend outwardly from an outer surface 152 of the wall 155, as shown in FIGS. 7 and 8, and engage the threads 127 and 128 disposed in the bore 126 of the inserter body 123.

The introducer hub 161 has first and second tabs 162 and 163, as shown in FIGS. 7 and 8. As shown in FIG. 7, first and second arms 181 and 182 extend downwardly from a first end 165 of the introducer hub 161. The first and second arms 181 and 182 extend substantially parallel to an outer surface 164 of the introducer hub 161. The second end 154 of the sleeve 151 abuts the first and second tabs 162 and 163 of the introducer hub 161, as shown in FIG. 7. The first end 165 of the introducer hub 161 is received by the sleeve 151, as shown in FIG. 8. The hollow introducer needle 167 extends from a second end 166 of the introducer hub 161 and is rigidly fixed thereto. Preferably, the introducer needle 167 is made of stainless steel.

Figure 19:
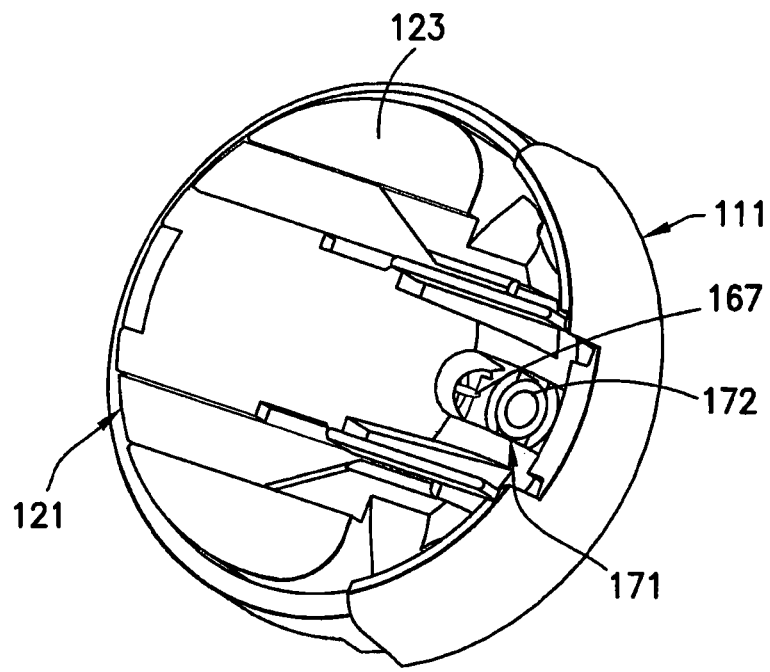
FIG. 19 is a perspective view of the inserter and base of FIG. 17.

A septum 172 is disposed inside a catheter hub 171, as shown in FIG. 7. The catheter hub 171 is disposed beneath the second end 166 of the introducer hub 161, as shown in FIG. 8. The soft catheter 173 extends downwardly from the catheter hub 172. The introducer needle 167 passes through the septum 172 and through the catheter 173 such that an end 168 of the introducer needle 167 is exposed outside of the catheter 173, as shown in FIG. 8, when the button 141 is in the first position. Preferably, the introducer needle end 168 is sharp to facilitate piercing the skin at a desired catheter insertion point. The septum 172 is inaccessible when the activation button 141 is in the first position as shown in FIG. 7, and accessible when the activation button 141 is in the second position as shown in FIG. 19.

Figure 6:
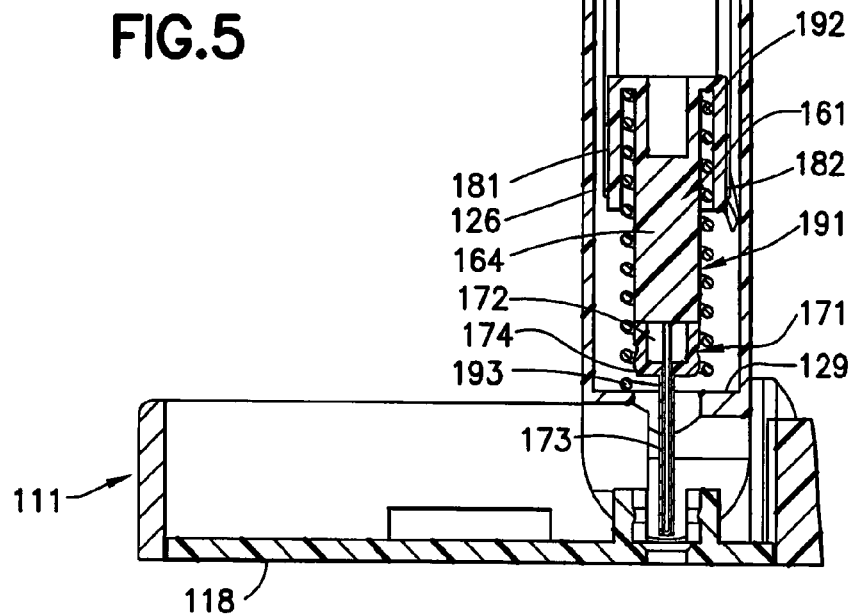
FIG. 6 is a side elevational view in cross-section of the inserter and base of FIG. 1.

A spring 191 is disposed on the outer surfaces 164 and 174 of the introducer hub 161 and the catheter hub 171, as shown in FIGS. 6 and 7. A first end 192 of the spring 191 is disposed proximal the first end 165 of the introducer hub 161. A second end 193 of the spring 191 is disposed at a shoulder 129 in the bore 126. Preferably, the spring 191 is a helical spring having a diameter larger than the portion of the bore beyond the shoulder 129 in which the introducer hub 161 is disposed. The first end 192 of the spring 191 is disposed between the outer surface 164 of the introducer hub 161 and the first and second arms 181 and 182 of the introducer hub 161.

A fluid connector 103 has first and second flexible arms 195 adapted to engage the first and second openings 104 and 105 in the base 111, as shown in FIGS. 20 and 21. Tubing 196 extends from the fluid connector 103 and is adapted to connect to a pump. The tubing 196 is connected to a penetrating member, or sharp, 197 extending downwardly from the fluid connector 103, and a fluid path is formed therebetween. The penetrating member 197 is adapted to penetrate the septum 172 when the fluid connector 103 is connected to the base 111, as shown in FIG. 21.

Assembly and Operation

FIG. 1 is a perspective view of the base 111 and folding inserter 121 as received by the user. The folding inserter 121 is pivotally connected to the base 111 by pins 108 and 109 to be pivotable about the projection 113, as shown in FIGS. 7, 9, 12 and 16. The folding inserter 121 is locked in a vertical, or first, position, with respect to the base 111, as shown in FIGS. 1, 2 and 7. The button 141 is in the up, or first, position relative to the inserter body 121, as shown in FIGS. 1 and 7. The fluid connector 103 (FIG. 20) is not yet connected to the base 111 because the soft catheter 173 has not yet been inserted. The soft catheter 173 and the introducer needle 167 are disposed within the base projection 113 and substantially entirely within the inserter body 123 in a first position, as shown in FIG. 7, such that accidental introducer needle sticks are substantially prevented. The first and second flexible arms 135 and 136 abut against an inner surface 112 of the wall 115 of the base, as shown in FIGS. 2 and 3, to prevent rotation of the folding inserter 121 to the second, or horizontal, position (FIGS. 17-19), thereby locking the inserter 121 in the first position.

The spring 191 is uncompressed when the inserter 121 is in the first position, as shown in FIGS. 6 and 7. The tabs 162 and 163 of the introducer hub 161 abut the second end 154 of the sleeve 151. The catheter hub 171 is disposed above the shoulder 129 of the bore 126. The sleeve tabs 157 and 158 are disposed at upper ends of the bore threads 127 and 128, as shown in FIG. 7, thereby preventing removal of the sleeve 151 from the inserter body 123.

Figures 11, 12:
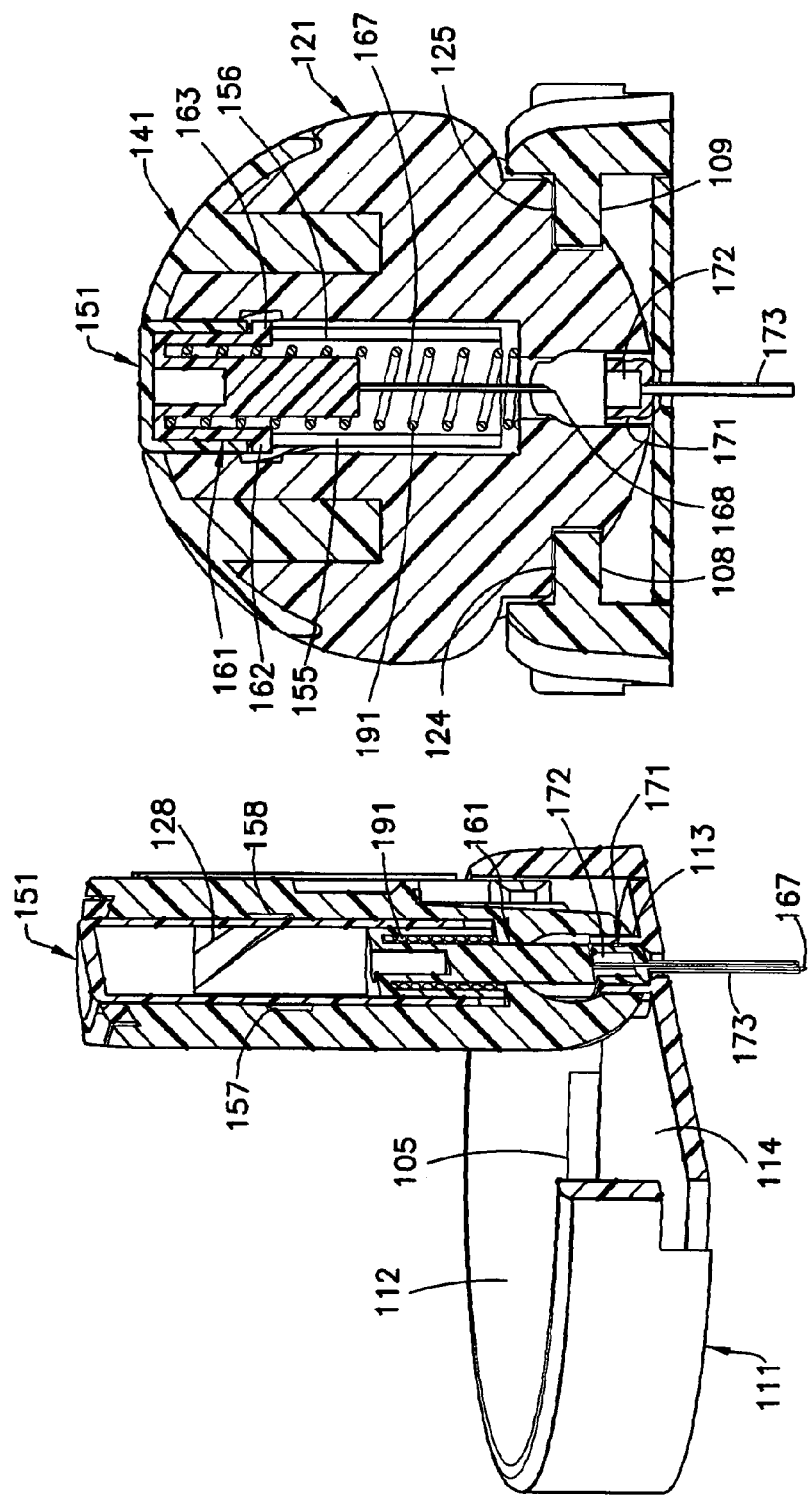
FIG. 11 is a perspective view in partial cross-section of the inserter and base of FIG. 9.
FIG. 12 is a front elevational view in cross-section of the inserter and base of FIG. 9 after withdrawing the introducer needle from the soft catheter.

Before inserting the catheter 173, the adhesive layer 110 is exposed and the base 111 positioned on the skin surface at the desired catheter insertion site. To insert the soft catheter 173, the activation button 141 is pressed inwardly until the activation button base 143 is flush with the folding inserter 121, as shown in FIGS. 9-11, thereby moving the activation button 141 from the first position to the second position. The sleeve 151 moves downwardly with the button 141, such that the sleeve tabs 157 and 158 move through the bore threads 127 and 128. The second end 154 of the sleeve 151 pushes the introducer hub 161 downwardly through engagement with the hub tabs 162 and 163. The downward movement of the introducer hub 161 compress the spring 191 between the shoulder 129 of the bore 126 and the introducer hub 161. The catheter hub 171 is also pushed downwardly by the introducer hub 161 such that the catheter hub 171 becomes mechanically connected to the projection 113 in the second position, as shown in FIGS. 9-11, thereby preventing upward movement of the catheter hub 171. Preferably, a snap fit is formed between the catheter hub 171 and the projection 113.

Figure 14:
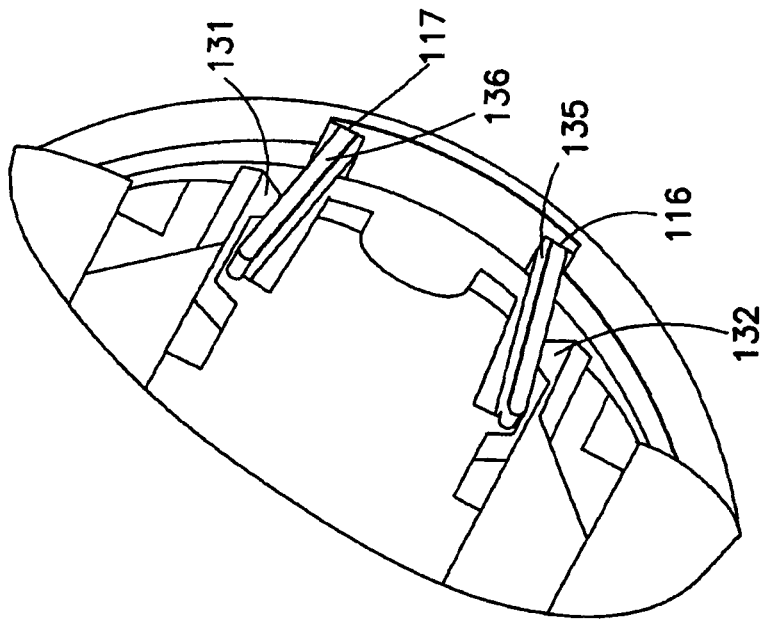
FIG. 14 is a partial enlarged perspective view of the activation button arms engaging the base arms of FIG. 13.
Figure 13:
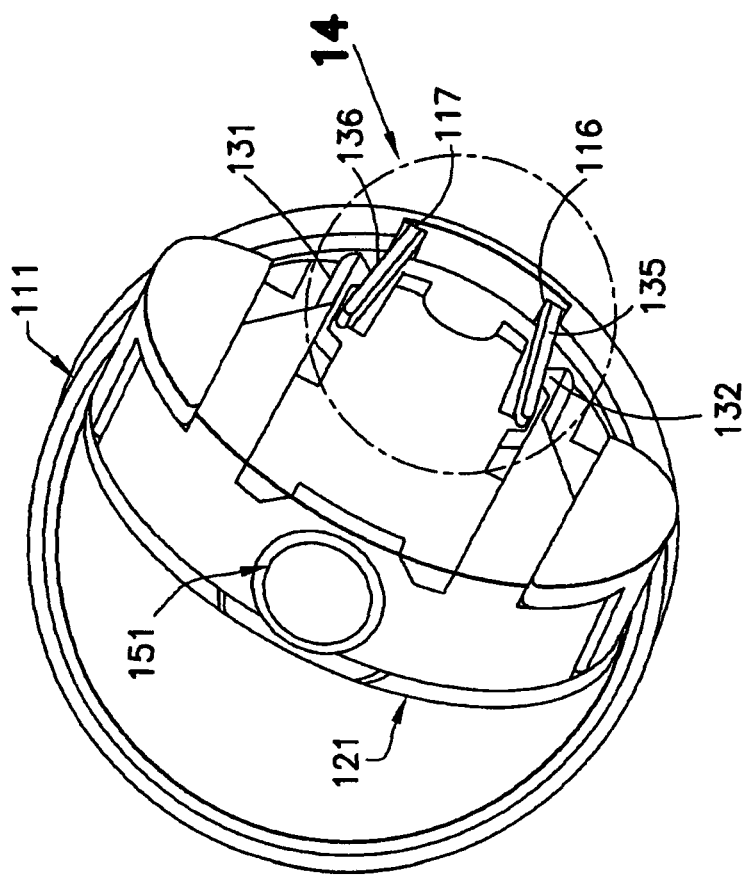
FIG. 13 is a perspective view of the inserter and base of FIG. 9 in which the activation button is in the depressed position.

The sleeve 151 rotates approximately 90 degrees through its downward motion by the sleeve tabs 157 and 158 traveling through the helical threads 127 and 128 of the bore 126 in the inserter body 123. Meanwhile, the first and second button flexible arms 131 and 132 engage the body flexible arms 135 and 136. The continued downward movement of the button arms 131 and 132 pushes the body arms 135 and 136 inwardly (toward one another), such that the body arms 135 and 136 move into the base grooves 116 and 117, as shown in FIGS. 13 and 14. As the body arms 135 and 136 no longer abut the wall 115 of the base 111, as shown in FIGS. 2 and 3, the inserter body 123 is now free to pivot due to the body arms 135 and 136 being disposed in the base grooves 116 and 117. The button posts 145 and 147 abut the bottom of the body cavities 120 and 122, thereby preventing further downward movement of the button 141. The downward movement of the introducer hub 161 causes the sharp end 168 of the introducer needle 167 to pierce the skin at the desired insertion site. The downward movement of the catheter hub 171 causes the catheter 173 to enter the skin substantially vertically through the pierced site.

As a result of the sleeve 151 rotation, the introducer hub tabs 162 and 163 are aligned with slots 155 and 156 in the sleeve 151. Consequently, the compression spring 191 is free to uncompress, driving the introducer hub 161 and the introducer needle 167 out of the skin of the patient, but leaving the catheter hub 171 fixed to the projection 113 and leaving the soft catheter 173 in the skin of the patient, as shown in FIG. 12. The compression spring 191 drives the introducer hub tabs 162 and 163 up through the slots 155 and 156 in the sleeve 151 back to the first position. The end 168 of the introducer needle 167 is retracted out of the septum 172 and catheter hub 171, as shown in FIG. 12.

Figure 16:
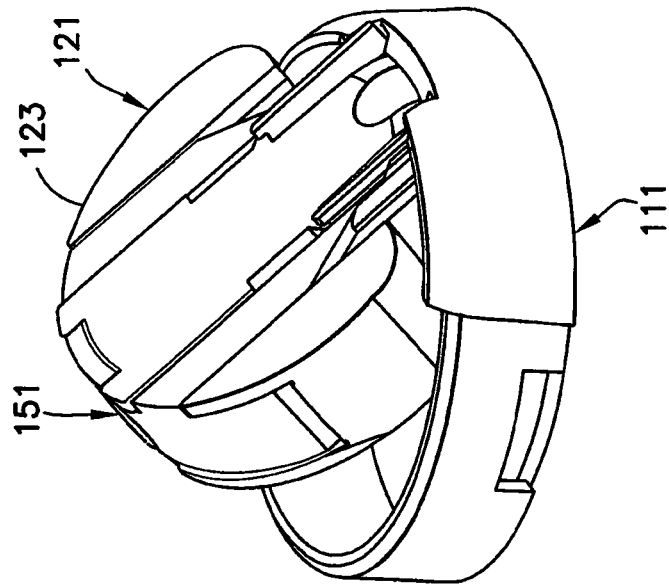
FIG. 16 is a perspective view of the inserter pivoting into the base of FIG. 1.
Figure 17:
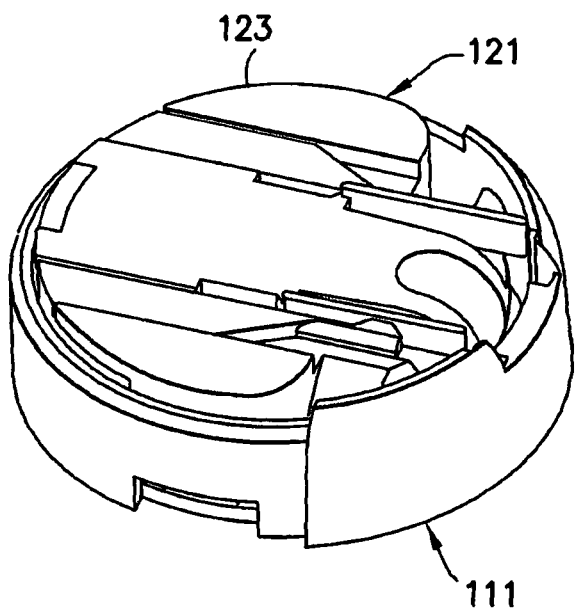
FIG. 17 is a perspective view of the inserter horizontally disposed in the base of FIG. 1.
Figure 18:
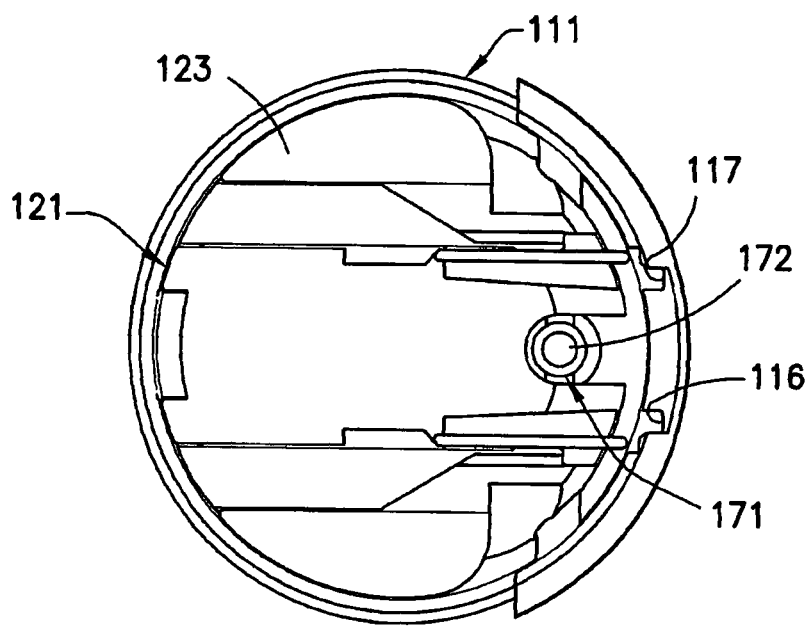
FIG. 18 is a top plan view of the inserter and base of FIG. 17.

The user can then rotate the inserter body 123, including the button 141, the sleeve 151, the introducer hub 161 and the introducer needle 167, as shown in FIG. 16, into the insertion set base 111, thereby storing the inserter 121 in a horizontal or second position, as shown in FIGS. 17-19. The inserter 121 is substantially entirely within the base 111. The septum 172 in the introducer hub 171 is now exposed, as shown in FIGS. 18 and 19. The soft catheter 173 remains inserted below the skin and in a substantially vertical position after the inserter body 123 has been rotated to the horizontal position, i.e., the soft catheter 173 does not bend with the pivotal movement of the inserter body 123. Accordingly, piercing the septum 172 provides a direct fluid path to the soft catheter 173 as the introducer needle 167 is not part of the fluid path.

A penetrating member, or sharp, 197 on the fluid connector 103 can now penetrate the septum 172, thereby creating a fluid connection between the catheter 173 and the tubing 196. The user can prime the fluid connector 103 prior to connecting it to the infusion set base 111. Flexible arms 195 of the fluid connector 103 engage openings 104 and 105 in the base 111 to removably connect the fluid connector 103 to the base 111. The infusion set 101, as shown in FIG. 21, is now ready to begin infusing insulin. The fluid connector 103 can be removed and reattached to the infusion set base 111 at any time by disengaging and connecting the flexible arms 195 with the base openings 104 and 105. The septum 172 provides a sterility barrier when the penetrating member 197 is removed therefrom, and the fluid connection is reestablished by reinserting the penetrating member 197 through the septum 172 located in the base 111.

The exemplary embodiment described above is usable for either intradermal or subcutaneous injections. A different method of maintaining the fluid connection is possible other than through the penetrating member 197 and septum 172. For example, a sliding gasket seal can be used. Alternative methods may be used to insert the catheter and introducer. For example, an angled needle in contact with the skin and driven horizontally can be used to enter the intradermal layer of the skin. Alternative methods of connecting the connector to the base can be used to facilitate connecting and disconnecting of the connector.

Although the exemplary embodiment described above is an infusion set, it will be apparent to those of ordinary skill in the art that the principles of the present invention are also applicable to patch pumps (self-contained infusion devices with integral reservoirs and pumping mechanisms) and other types of medical infusion and injection devices.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. An infusion set, comprising:
a base; and
an inserter pivotally connected to said base and configured to fold substantially entirely within said base, said inserter including:
  a catheter movable from a first catheter position disposed substantially entirely within said inserter to a second catheter position in which a free end of said catheter is disposed externally of said inserter and said base;
  an introducer needle located within said catheter and movable between a first introducer needle position disposed substantially entirely within said inserter and a second introducer needle position in which a free end of said introducer needle is disposed externally of said inserter and said base; and
  an activation button movable between first and second button positions, wherein when said button is moved from said first button position to said second button position, said catheter is moved from said first to said second catheter position, said introducer needle is moved from said first to said second introducer needle position to facilitate insertion of said catheter, and said introducer needle is thereafter moved back toward said first introducer needle position to store said introducer needle within said inserter with said free end of said catheter remaining disposed externally of said inserter and said base.

2. The infusion set in accordance with claim 1, wherein a fluid connector is removably connected to said base and connectable to a medicament source.

3. The infusion set in accordance with claim 2, wherein said fluid connector has a penetrating member to pierce a septum in said base to create a fluid connection between said catheter and the medicament source when said fluid connector is connected to said base.

4. The infusion set in accordance with claim 2, wherein said inserter is pivotable between a first inserter position for inserting said introducer needle and said catheter and a second inserter position in which said inserter is disposed substantially entirely within said base.

5. The infusion set in accordance with claim 4, wherein said inserter is substantially perpendicular to said base in said first inserter position.

6. The infusion set in accordance with claim 5, wherein said introducer needle and said catheter enter a skin surface at a substantially perpendicular angle to the skin surface.

7. The infusion set in accordance with claim 4, wherein said septum is inaccessible when said inserter is in said first inserter position and exposed when said inserter is in said second inserter position.

8. An infusion set, comprising:
a base; and
an inserter pivotally connected to said base, said inserter including:
  a body pivotable between first and second body positions;
  a sleeve disposed in said inserter body for movement linearly and rotationally between first and second sleeve positions;
  a catheter hub movable from a first catheter hub position to a second catheter hub position;
  a catheter connected to said catheter hub, said catheter being disposed substantially entirely within said inserter body when said catheter hub is in said first catheter hub position and said catheter having a free end disposed externally of said inserter body and said base when said catheter hub is in said second catheter hub position;

an introducer hub movable between a first introducer hub position and a second introducer hub position;

an introducer needle located within said catheter and connected to said introducer hub, said introducer needle being disposed substantially entirely within said inserter body when said introducer hub is in said first introducer hub position and said introducer needle having a free end disposed externally of said inserter body and said base when said introducer hub is in said second introducer hub position; and an activation button movable between first and second button positions, wherein when said button is in said first button position, said catheter hub and said introducer hub are in said first catheter hub position and said first introducer hub position, respectively; when said activation button is between said first and second button positions, said sleeve moves linearly and rotationally from said first sleeve position to said second sleeve position and said catheter hub and said introducer hub are moved to said second catheter hub position and said second introducer hub position, respectively; and when said activation button is in said second button position, said catheter hub is in said second catheter hub position and said sleeve releases said introducer hub to retract toward said first introducer hub position.

9. The infusion set in accordance with claim 8, wherein a fluid connector is removably connected to said base and connectable to a medicament source.

10. The infusion set in accordance with claim 8, wherein a spring member biases said introducer hub toward said first introducer hub position.

11. The infusion set in accordance with claim 10, wherein first and second tabs on said sleeve engage grooves in said inserter body to guide axial and rotational movement of said sleeve when said sleeve is moved from said first sleeve position to said second sleeve position by said activation button.

12. The infusion set in accordance with claim 11, wherein first and second tabs on said introducer hub are engaged by said sleeve to move said introducer hub from said first introducer hub position to said second introducer hub position when said sleeve is moved from said first sleeve position to said second sleeve position.

13. The infusion set in accordance with claim 12, wherein said first and second introducer hub tabs engage slots in said sleeve when both said sleeve and said introducer hub are in their respective second positions such that said spring member returns said introducer hub and said introducer needle toward their respective first positions.

14. The infusion set in accordance with claim 13, wherein said catheter hub engages a protrusion on said base to retain said catheter hub in said second catheter hub position.

15. The infusion set in accordance with claim 14, wherein flexible arms on said inserter body engage said base to lock said inserter body in said first body position.

16. The infusion set in accordance with claim 15, wherein said introducer needle and said catheter enter a skin surface at a substantially perpendicular angle to the skin surface.

17. The infusion set in accordance with claim 16, wherein a septum is disposed in said catheter hub.

18. The infusion set in accordance with claim 17, wherein said septum is inaccessible when said inserter body is in said first body position and exposed when said inserter body is in said second body position.

19. A method of inserting a catheter of an infusion set, comprising the steps of:

disposing the infusion set on a skin surface at an injection site;

inserting an introducer needle and the catheter through the skin surface with an inserter of the infusion set;

removing the inserted introducer needle from the skin surface;

storing the removed introducer needle substantially entirely within the inserter; and pivoting the inserter from a substantially vertical to a substantially horizontal position to store the inserter within a base of the infusion set.

20. The method of inserting a catheter of an infusion set in accordance with claim 19, wherein the removed introducer needle is not part of a fluid path between the inserted catheter and a medicament source.

\* \* \* \* \*